US007198045B2

(12) United States Patent
Risley et al.

(10) Patent No.: US 7,198,045 B2
(45) Date of Patent: Apr. 3, 2007

(54) LOW PRESSURE HYPERBARIC CHAMBER AND METHOD OF USING THE SAME

(76) Inventors: Hollis Parker Risley, 8061 Fountains La., Destin, FL (US) 32550; Maurice Ernest Parks, 2912 Loblolly Ct., Destin, FL (US) 32550

( * ) Notice: Subject to any disclaimer, the term of this patent is extended or adjusted under 35 U.S.C. 154(b) by 0 days.

(21) Appl. No.: 10/365,633

(22) Filed: Feb. 10, 2003

(65) Prior Publication Data

US 2004/0154616 A1 Aug. 12, 2004

(51) Int. Cl.
*A61G 10/00* (2006.01)
*A61M 16/00* (2006.01)

(52) U.S. Cl. ............................ 128/202.12; 128/204.18

(58) Field of Classification Search ........... 128/200.24, 128/205.26, 205.28, 202.12–202.14, 201.27, 128/204.18, 204.23; 600/21, 22; 482/13, 482/148; 405/186, 187, 192; 52/2.11, 2.12, 52/2.14, 2.17; 454/187, 238; 55/385.2

See application file for complete search history.

(56) References Cited

U.S. PATENT DOCUMENTS 3,744,491 A * 7/1973 Fischer ........................ 604/23
3,766,844 A * 10/1973 Donnelly et al. ........... 454/238
4,103,369 A * 8/1978 Riordan ...................... 52/2.14
4,509,513 A * 4/1985 Lasley ................... 128/202.12
4,707,953 A * 11/1987 Anderson et al. .............. 52/63
5,152,814 A 10/1992 Nelson
5,255,673 A * 10/1993 Cardwell et al. ...... 128/202.12
5,360,001 A 11/1994 Brill et al.
5,467,764 A * 11/1995 Gamow ................. 128/202.12
5,478,310 A * 12/1995 Dyson-Cantwell et al. ... 604/23
5,503,143 A * 4/1996 Marion et al. ......... 128/202.12
5,537,784 A * 7/1996 Baldwin ..................... 52/2.17
5,630,296 A * 5/1997 Kendall, Jr. ...................... 52/2
5,776,048 A * 7/1998 Jo .............................. 600/21
5,810,795 A * 9/1998 Westwood .................. 604/305
5,865,722 A * 2/1999 Heng .......................... 600/21
5,964,065 A * 10/1999 Migurski et al. .............. 52/64
RE36,958 E * 11/2000 Gamow ................. 128/202.21
6,199,551 B1 * 3/2001 Kuslich ................ 128/205.26
6,217,507 B1 * 4/2001 Bonvik ........................ 600/21
6,321,764 B1 * 11/2001 Gauger et al. .............. 135/128
6,508,850 B1 * 1/2003 Kotliar ...................... 55/385.2
6,572,594 B2 * 6/2003 Satterfield et al. .......... 604/290
6,623,351 B2 * 9/2003 Brown ....................... 454/187

FOREIGN PATENT DOCUMENTS

GB 1027114 4/1966
WO WO 02/069876 A1 9/2002

OTHER PUBLICATIONS

Anesthesia Z; Magazine; pp. 1-5.*
HBO Hyperbaric Oxygen (www.anestodya.com/Magazine/AnesA-Z/atoz-h.htm.*
A Brief Review of Hyperbaric Oxygen for Stroke Rehabilitation, David A. Steenblock, M.S., D.O.*

* cited by examiner

*Primary Examiner*—Teena Mitchell
(74) *Attorney, Agent, or Firm*—Winstead Sechrest & Minick P.C.

(57) ABSTRACT

A low pressure hyperbaric chambers and methods of using same are disclosed. The present invention provides means for designing, building, and using low pressure chambers suitable for use in managing pain associated with medical conditions.

24 Claims, 3 Drawing Sheets

LOW PRESSURE HYPERBARIC CHAMBER AND METHOD OF USING THE SAME

FIELD OF INVENTION

The present invention relates to the construction and use of low pressure hyperbaric chambers, and more specifically, to the construction of chambers to provide an air pressure of greater than approximately 30.1 in. Hg, and the use of such chambers in the treatment of pain and other symptoms of chronic disease.

BACKGROUND OF INVENTION

Many people suffer from pain and other symptoms of chronic conditions. For example, diseases such as rheumatoid arthritis, lupus, fibromyalgia, and other similar diseases often cause severe, debilitating, chronic pain. Often the only treatment is through the use of expensive medications with undesirable side effects.

It would therefore be desirable to provide methods and apparatus for treating the pain and other symptoms associated with chronic diseases.

It would also be desirable to provide methods and apparatus for treating pain and other symptoms associated with chronic diseases at reduced cost.

It is also desirable to reduce or eliminate the medicaments needed to treat pain and other symptoms associated with chronic diseases.

SUMMARY OF INVENTION

These and other objects and advantages of the present invention are provided by a hyperbaric chamber that subjects the user to an atmospheric pressure of approximately 30.1 to 32 in. Hg.

In a first, portable, embodiment of the present invention, the chamber is made of a substantially air-tight material. A centrifugal blower provides a sufficient air flow to inflate the chamber and provide the desired air pressure in the chamber. Preferably, the chamber includes an air lock to enable a user to enter or exit the chamber without it deflating. Air leakage through seams and zippers in the chamber ensure an adequate turn-over rate of the air in the chamber.

In a second embodiment of the hyperbaric chamber, in accordance with the principles of the present invention, the chamber is made of a hard material such as fiberglass, wood, metal or plastic, and is sized to accommodate home use. For example, the chamber may be designed to fit in a closet or other small room. As in the portable embodiment of the hyperbaric chamber, a centrifugal fan provides the desired air pressure and air flow.

In yet a third embodiment of the present invention, the chamber is made large enough for clinical use. Preformed panels of laminated aluminum honeycomb, or similar material, are bolted together with appropriate gaskets to create a chamber of a desired size. One or more centrifugal blowers provide air pressure and small openings in the structure ensure air flow requirements are met. An air lock may be provided to enable user entry with out a loss of pressure.

BRIEF DESCRIPTION OF DRAWINGS

For a more complete understanding of the present invention, and the advantages thereof, reference is now made to the following descriptions taken in conjunction with the accompanying drawings, in which like reference characters refer to like parts throughout, and in which.

DETAILED DESCRIPTION OF THE INVENTION

The present invention is a means of providing an atmospheric pressure analogous to the pressure one would experience in a meteorological high pressure area. For example, the present invention provides cost effective means to produce and subject a user to a pressure greater than approximately 30.1 and preferably less than about 32.0 in. Hg. Moreover, the present invention provide a method of using increased atmospheric pressure to reduce or eliminate the pain and other symptoms associated with many chronic diseases.

Figure 1:
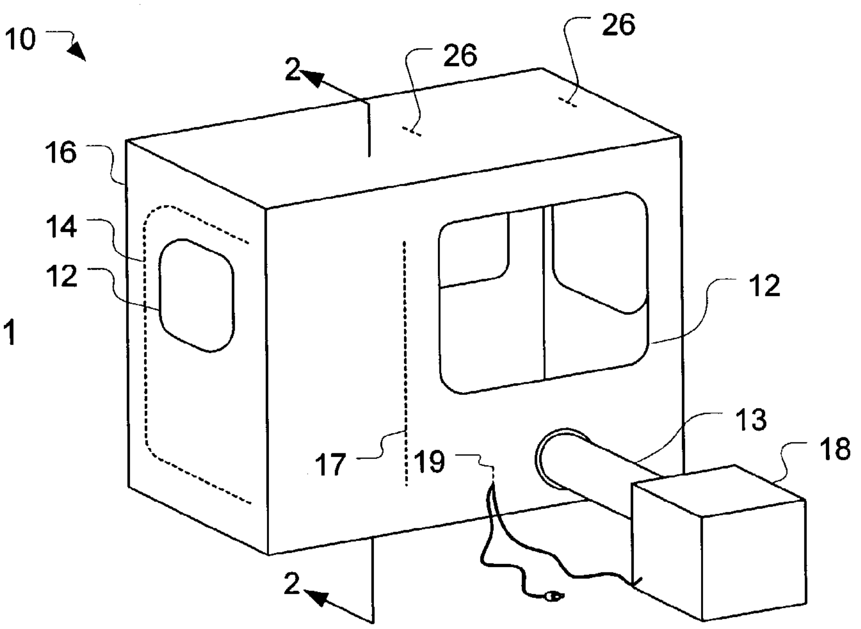
FIG. 1 is a simplified drawing of a portable inflatable hyperbaric chamber in accordance with the principles of the present invention.

Referring first to FIG. 1, an exemplary embodiment of portable hyperbaric chamber 10 is described. Portable hyperbaric chamber 10 is an inflatable structure constructed of a fabric or material that is flexible and sufficiently air-tight. For example, 18 ounce vinyl-coated fabric, or other suitable material, may be used to construct chamber 10. Panels of the material are cut to size and stitched or seam welded to each other to create the chamber. The panels may include windows 12 made of clear vinyl or other plastic. Preferably, chamber 10 is large enough for a user to sit or stand comfortably inside.

Chamber 10 is inflated by fan or blower 18, which is coupled to chamber 10 by means of flexible hose, or ducting 13, preferably made of the same material as chamber 10. Blower 18 provides air at a sufficient volume and pressure to inflate chamber 10 and provide an internal pressure between about 30.1 and about 32 in. Hg. For example, a centrifugal fan delivering an air flow of approximately 600 cubic feet per minute (CFM) at 4 to 6 in. Hg. is sufficient to inflate chamber 10. Zippered access 19 is provided for external services and utilities. For example, a telephone cord may be passed through zipper 19 so that a user of chamber 10 has access to a telephone.

Figure 2:
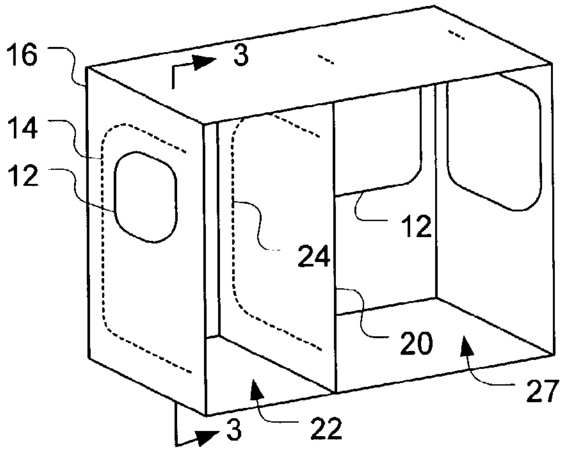
FIG. 2 is a cutaway view of the chamber of FIG. 1.
Figure 3:
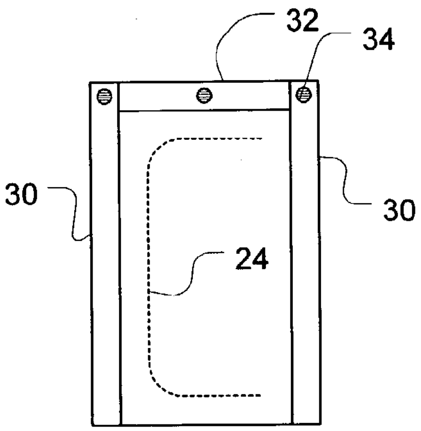
FIG. 3 is a front sectional view of the airlock portion of the hyperbaric chamber of FIG. 1.

As shown in FIG. 2, chamber 10 includes internal wall 20 to form airlock 22. Zipper 14 in end panel 16 provides a sealable flap that is used for entry into airlock 22. Zipper 24 provides for passage between airlock 22 and inner chamber 27. To ensure airlock 22 does not collapse when zipper 14 is opened, airlock 22 includes internal structural members. Preferably, inflatable columns, pillars, or walls, are provided in the corners, walls, and overhead of airlock 22 to provide support for airlock 22 when zipper 14 is open. The inflatable structural members are connected to and receive pressure from inner chamber 27. For example, in FIG. 3, exterior walls 30 and ceiling 32 of airlock 22 are of double wall construction and the space within walls 30 and ceiling 32 are connected to inner chamber 26 through openings 34. Alternatively, collapsible rods or the like may be used to support the walls and ceiling of hyperbaric chamber 10 when blower 18 is off.

To ensure adequate oxygen for the occupant of chamber 10, the air within chamber 10 should be changed at a rate of approximately 30 CFM per person. Typically, air leakage through the seams between the panels of chamber 10 and through zippers 14, 19, and 24 is sufficient to ensure adequate airflow; however, zippers 26 may be opened to increase airflow if needed. If blower 18 stops, e.g., because of a power failure, the air leakage from chamber 10 is slow enough that a user of chamber 10 has several minutes to exit from the chamber through airlock 22 before the chamber has deflated. However, zipper 17 may be provided as an alternate means of directly exiting from inner chamber 26 in an emergency.

Figure 4:
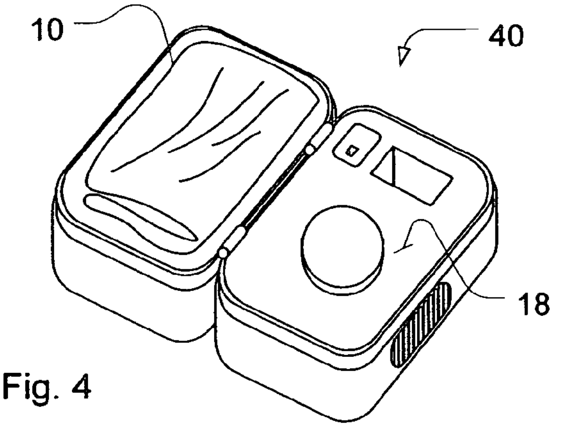
FIG. 4 is a perspective view of a case for holding the chamber of FIG. 1 during storage or transportation.

Because chamber 10 is made of a flexible material, it may be folded to a relatively compact size when not in use or when traveling. In a preferred embodiment, blower 18 is built into one side of a hard sided equipment case, such as hard case 40 shown in FIG. 4. Chamber 10 may then be folded and stored in the other side of hard case 40. Although they are not shown in FIG. 4, case 40 may also be provided with casters or wheels and a telescoping handle similar to that found on conventional luggage. Alternatively, chamber 10 may be folded and stored in a separate case from blower 18.

Figure 5:
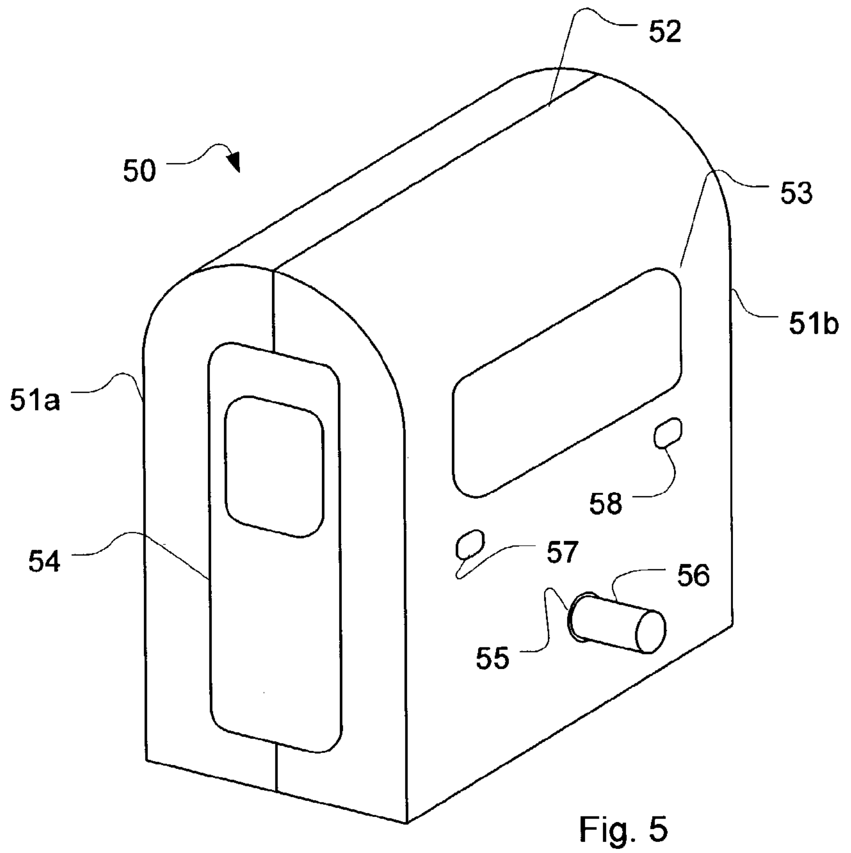
FIG. 5 is a simplified drawing of a small hyperbaric chamber suitable for home use in accordance with the principles of the present invention.

A second embodiment of a hyperbaric chamber constructed in accordance with the principles of the present invention is shown in FIG. 5, wherein chamber 50 is suitable for a relatively permanent installation in a home or office. Preferably, chamber 50 is made in two halves molded from fiberglass or other suitable material and is approximately the size of a shower stall or large closet. Fiberglass halves 51*a* and 51*b* include a flange 52 for bolting the two halves together. A gasket or chalking between the two halves provides an air seal. Plexiglas windows 53 are set into chamber halves 51*a* and 51*b* with a suitable grooved gasket. Hinged entry door 54, also made of fiberglass, has a flange that mates to the opening in the end of chamber 50. A self adhesive rubber or foam gasket minimizes air leakage around door 54.

Although it is not shown in FIG. 5, chamber halves 51*a* and 51*b*, and door 54 may include ribs or other structures designed to stiffen the chamber components and minimize ballooning of the chamber sides. Chamber side 51*b* includes a flanged opening 55 for connecting to a blower using a flexible hose or rigid duct work 56. Access port 57 is used for mechanical and electrical services, such as to provide power for a lamp, or a telephone outlet. Vent 58 ensures airflow is adequate.

Figure 6:
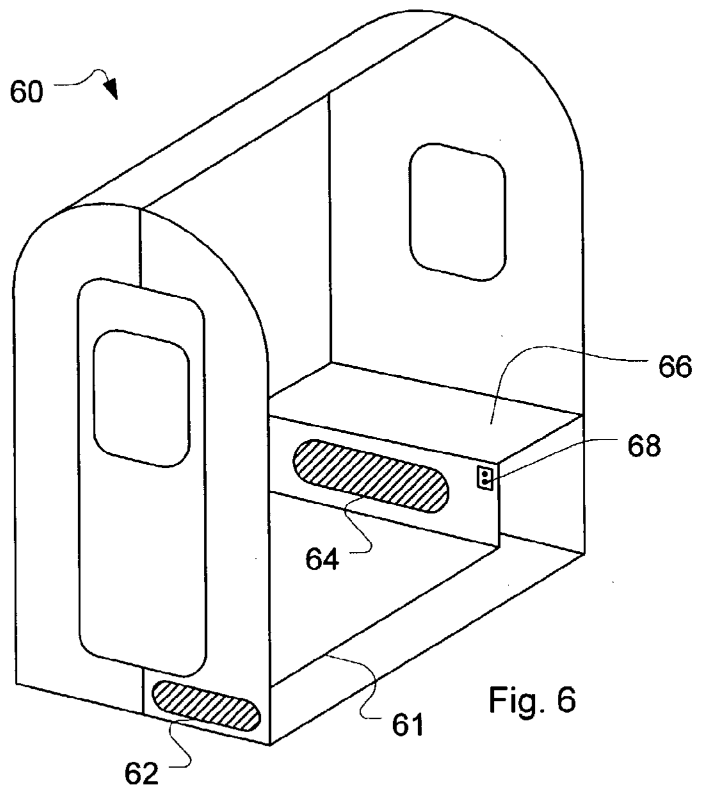
FIG. 6 is an alternative embodiment of the chamber of FIG. 5.

Alternatively, the hyperbaric chamber may include suitable ducting so that the blower may be located inside the chamber. For example, chamber 60 in FIG. 6 includes a double floor system configured so that outside air is drawn into the blower through opening 62 and discharged into chamber 60 through outlet 64 on the front of bench 66. Power switch 66 controls a blower located under bench 66.

Figure 7:
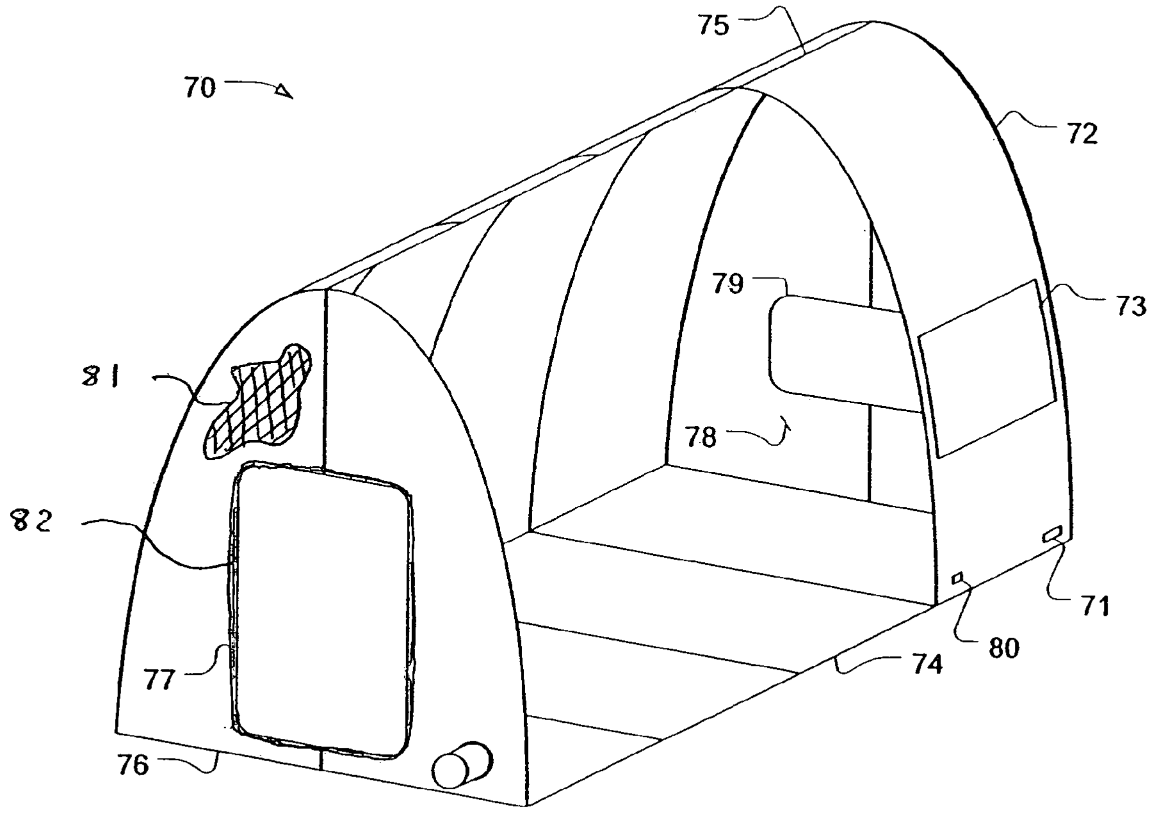
FIG. 7 is a simplified view of a hyperbaric chamber suitable for clinical use.

A larger chamber, suitable for clinical use in a medical office, hospital, or other treatment facility is shown in FIG. 7. Chamber 70 is significantly larger that the chambers of FIGS. 1 through 6, and may be designed to hold several people at once, including patients and medical care givers. Preferably, chamber 70 is modular in design, so that it can be made in various sizes, and made of components that are small enough to be easily transported and assembled. Accordingly, chamber 70 is constructed of a number of preformed panels for the walls, floors and ends of the chamber. Each panel has a flange so that it can be bolted or otherwise attached to an adjoining panel. A gasket or caulking is used between adjacent panels for an air seal. Preferably, the panels are made of a rigid material, such as a laminate of aluminum with a honeycomb core (shown generally by the cut-away portion of FIG. 7 at designator 81), to minimize ballooning of the chamber. Alternatively, a composite material such as fiberglass with ribs and other structural reinforcements may be used.

Chamber 70 of FIG. 7 includes panels 72 to form the sides and ceiling of the chamber. Side panels 72 include openings or penetrations 71 for utility connections and openings for Plexiglas windows 73. Pairs of panels 72 connect at flanged joint 75 and to floor panels 74 to form an arch-shaped section of the chamber. Multiple sections are combined to make the chamber the desired size. End panels 76 and 78 complete the structure. End panels 76 include an opening for hinged Plexiglas door 77 and end panel 78 has a cutout for window 79. If desired, an additional end panel 76 and door 77 may be inserted between two adjacent arch-shaped sections to form an airlock. Gasket material 82 provides a seal between door 77 and adjacent end panel 76.

Air is supplied to chamber 70 through suitable duct work fastened to a flange in a side panel 72 or end panel 76 or 78, similar to that shown in FIG. 5. Alternatively, the blower may be located internally in a fashion analogous to chamber 60 in FIG. 6. Because of the increased size of chamber 70 a 1200 CFM centrifugal fan is used. Alternatively, multiple smaller blowers may be used. Openings 80 ensure an adequate turn over rate of the air in chamber 70.

METHOD OF USE

The inventors have determined that spending time in a hyperbaric chamber at an air pressure of approximately 30.1 to 32 in. Hg provides extended relief from chronic pain and other symptoms associated with a number of diseases, including rheumatoid arthritis, lupus, fibromyalgia, asthma and others. Based on initial testing, users of the chambers report relief lasting for an extended period after a relatively brief session in the chamber. The degree and duration of relief obtained varies for each user, so that some degree of experimentation is required to determine a regimen that optimizes relief.

As an example, one test subject reports that two 30 minute sessions, one in the morning and one in the evening, provides enough relief from joint pain associated with rheumatoid arthritis that pain medications are no longer needed. An asthmatic user has reported improved breathing as a result of using a hyperbaric chamber of the present invention and a user with circulation problems has experienced a reduction in leg pain following treatment. Other users of the chambers report similar relief from the symptoms associated with their diseases.

Thus, low pressure hyperbaric chambers and methods of using the same are disclosed. The specific arrangements and methods are described herein in terms of several preferred embodiments which are provided for purposes of illustration and not of limitation. Numerous modifications in form and detail may be made by those of ordinary skill in the art without departing from the invention in its broader aspects, and, therefore, the aim in the appended claims is to cover all such changes and modifications as fall within the true spirit and scope of the invention.

What is claimed is:

1. A low pressure hyperbaric chamber for treating a chronic ailment comprising:

a structure having a plurality of surfaces, the structure allowing airflow therethrough;

a closable opening for providing access to the chamber; and an air blower of sufficient capacity to pressurize the volume of the structure, with airflow through the structure, to a pressure of greater than about 30.1 in. Hg and less than about 32.0 in. Hg for treating a chronic ailment of a user accommodated within the chamber;

wherein said air blower has sufficient capacity to provide at least 30 CFM airflow; and wherein said airflow provides for adequate turn-over rate of air within said hyperbaric chamber.

2. The chamber of claim 1, wherein the surfaces are made of a flexible material and the air blower has sufficient capacity to inflate the chamber.

3. The chamber of claim 2, wherein the chamber includes an air lock for entry to or exit from the chamber may be made without a loss of pressure in the chamber.

4. The chamber of claim 2, wherein the flexible material is a vinyl coated fabric.

5. The chamber of claim 4, wherein the opening comprises a zippered flap.

6. The chamber of claim 2, wherein the chamber is collapsible so that it is portable.

7. The chamber of claim 1, wherein the surfaces are made of a rigid material so that the chamber retains its shape when the air blower is off.

8. The chamber of claim 7, wherein the rigid material comprises fiberglass or plastic.

9. The chamber of claim 7, wherein the rigid material comprises a laminate with a honeycomb core.

10. The chamber of claim 7, wherein the surfaces comprise preformed parts that are coupled together to form the chamber.

11. The chamber of claim 10, wherein at least one of the preformed parts include an opening for a door or window.

12. The chamber of claim 7, wherein the chamber comprises:

a door in at least one surface for entry into the chamber, the door including a portion for mating with a portion of at least one surface; and gasket material for providing a seal between the door and the portion of the at least one surface.

13. The device of claim 1 wherein said ailment is chosen from the group consisting of fibromyalgia, rheumatoid arthritis and osteoarthritis.

14. The device of claim 1 wherein said airflow is outside air drawn into the blower.

15. The device of claim 1 wherein the chamber is designed to hold several people and the airflow is at least 30 CFM per person.

16. A method of using a low pressure hyperbaric chamber for treating a chronic ailment, the method comprising:

occupying the chamber; and pressurizing, with airflow through the chamber, the chamber to between about 30.1 and 32.0 in. Hg for treating a chronic ailment of a patient accommodated within the chamber;

wherein said airflow is at least about 30 CFM per user in the chamber; and wherein said airflow provides for adequate turn-over rate of air within said hyperbaric chamber.

17. The method of claim 16 further comprising inflating the chamber prior to occupying the chamber.

18. The method of claim 17 further comprising deflating the chamber after occupying the chamber.

19. The method of claim 16 further comprising remaining in the pressurized chamber for between about 20 and about 60 minutes.

20. The method of claim 19 further comprising occupying the chamber in the morning and in the evening.

21. The method of claim 16 further comprising occupying the chamber at least twice a day.

22. The method of claim 16 wherein said ailment is chosen from the group consisting of fibromyalgia, rheumatoid arthritis and osteoarthritis.

23. The method of claim 16 wherein said airflow is outside air drawn into the blower.

24. The method of claim 16 wherein several people are accommodated within the chamber.

* * * * *